United States Patent
Smieszek et al.

(10) Patent No.: US 11,607,408 B2
(45) Date of Patent: Mar. 21, 2023

(54) METHOD OF TREATMENT OF SCHIZOPHRENIA

(71) Applicant: Vanda Pharmaceuticals Inc., Washington, DC (US)

(72) Inventors: Sandra Smieszek, Cleveland, OH (US); Mihael H. Polymeropoulos, Potomac, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 35 days.

(21) Appl. No.: 17/070,622

(22) Filed: Oct. 14, 2020

(65) Prior Publication Data
US 2021/0106575 A1    Apr. 15, 2021

Related U.S. Application Data

(60) Provisional application No. 62/915,395, filed on Oct. 15, 2019.

(51) Int. Cl.
| | |
|---|---|
| *A61K 31/454* | (2006.01) |
| *A61K 45/06* | (2006.01) |
| *A61K 31/451* | (2006.01) |
| *A61K 31/5415* | (2006.01) |
| *A61P 25/18* | (2006.01) |

(52) U.S. Cl.
CPC .......... *A61K 31/454* (2013.01); *A61K 31/451* (2013.01); *A61K 31/5415* (2013.01); *A61K 45/06* (2013.01); *A61P 25/18* (2018.01)

(58) Field of Classification Search
CPC ............... A61K 31/451; A61K 31/454; A61K 31/5415; A61P 25/18
See application file for complete search history.

(56) References Cited

U.S. PATENT DOCUMENTS

| | | |
|---|---|---|
| 5,776,963 A | 7/1998 | Strupczewski et al. |
| RE39,198 E | 7/2006 | Strupczewski et al. |
| 7,767,230 B2 | 8/2010 | Ahlheim et al. |
| 8,227,488 B2 | 7/2012 | Wieckhusen et al. |
| 8,293,765 B2 | 10/2012 | Wieckhusen et al. |
| 8,586,610 B2 | 11/2013 | Wolfgang et al. |
| 8,614,232 B2 | 12/2013 | Wieckhusen et al. |
| 8,815,293 B2 | 8/2014 | Ahlheim et al. |
| 8,999,638 B2 | 4/2015 | Wolfgang et al. |
| 9,080,214 B2 | 7/2015 | Lavedan et al. |
| 9,138,432 B2 | 9/2015 | Wolfgang et al. |
| 9,157,121 B2 | 10/2015 | Wolfgang et al. |
| 9,328,387 B2 | 5/2016 | Lavedan et al. |
| 9,458,507 B1 | 10/2016 | Lavedan et al. |

FOREIGN PATENT DOCUMENTS

WO    2003020707 A1    3/2003

OTHER PUBLICATIONS

Gray et. al., Int. J. of Neuropsychopharm., vol. 12, pp. 45-60, publ. 2008 (Year: 2008).*
Timms, Andrew E. et al.; "Support for the N-Methyl-D-Aspartate Receptor Hypofunction Hypothesis of Schizophrenia From Exome Sequencing in Multiplex Families"; JAMA Psychiatry; vol. 70; No. 6; pp. 582-590; Jun. 2013.
Patel, Krishna et al.; "Schizophrenia: Overview and Treatment Options"; P&T; vol. 39; No. 9; pp. 638-645; Sep. 2014.

* cited by examiner

*Primary Examiner* — Sarah Pihonak
(74) *Attorney, Agent, or Firm* — Hoffman Warnick LLC

(57) ABSTRACT

The invention relates generally to improvements in the treatment of psychotic symptoms, and more particularly, to improvements in the identification of an individual or a population of individuals for whom treatment with iloperidone, an iloperidone metabolite, or pharmaceutically-acceptable salts thereof may provide a particular benefit in treating an individual's psychotic symptoms based on the individual's genotype at the PPEF2 locus.

23 Claims, 3 Drawing Sheets

METHOD OF TREATMENT OF SCHIZOPHRENIA

CROSS REFERENCE TO RELATED APPLICATION

This patent application claims the benefit of U.S. provisional patent application Ser. No. 62/915,395, filed Oct. 15, 2019, the contents of which are incorporated herein as though fully set forth.

BACKGROUND OF THE INVENTION

The invention relates generally to improvements in the treatment of psychotic symptoms, and more particularly, identifying individuals or a population of individuals for whom treatment may provide a particular benefit in treating an individual's psychotic symptoms based on the individual's genotype at the PPEF2 locus.

Schizophrenia is a psychotic disorder affecting between about 0.6% and 1.9% of the US population. It is characterized by the presence of positive symptoms (e.g., hallucinations and delusions) and negative symptoms (e.g., blunted affect and social withdrawal), as well as impairment of cognitive functions (e.g., verbal memory, information processing). The nature and severity of an individual's schizophrenia may be measured using a number of scales, the most widely used being the Positive and Negative Syndrome Scale (PANSS). A number of PANSS subscales may also be used, such as the PANSS general psychopathology subscale (PANSS-GP), the PANSS positive symptom subscale (PANSS-P), and the PANSS negative symptom subscale (PANSS-N). The PANSS total score (PANSS-T) is comprised of all PANSS subscales.

There is much evidence that schizophrenia may not be caused by a single major gene, but rather is a complex genetic disorder with a multifactorial mode of inheritance. Genetic studies have implicated many different genes and pathways, but much of the genetic liability is still unaccounted for. Leading theories of the pathophysiology of schizophrenia include the glutamate and dopamine pathways. Glutamate is the major excitatory neurotransmitter in the nervous system.

A number of drugs have been approved to treat schizophrenia. However, patient response to treatment remains highly variable, and the discontinuation rate with antipsychotic treatment is high. No single antipsychotic agent offers optimal effect for every patient with schizophrenia. Few data are available to guide clinicians and patients in the selection of the most appropriate medication, and in the improvement of treatment specificity for an individual patient.

Iloperidone (1-[4-[3-[4-(6-flouro-1,2-benzisoxazol-3-yl)-1-piperidinyl]propoxy]-3-methoxyphenyl]ethanone) is an atypical antipsychotic disclosed in U.S. Pat. RE39198. Metabolites of iloperidone, e.g., P88 (also referred to as P-88-8891 or 1-[4-[3-[4-(6-fluoro-1,2-benzisoxazol-3-yl)-1-piperidinyl]propoxy]-3-methoxyphenyl]ethanol), are also useful in the present invention. See, e.g., International Patent Application Publication No. WO03020707, which is incorporated herein by reference. Other iloperidone metabolites include: 1-[4-[3-[4-(6-fluoro-1,2-benzisoxazol-3-yl)-1-piperidinyl]propoxy]-3-hydroxyphenyl]ethanone; 1-[4-[3-[4-(6-fluoro-1,2-benzisoxazol-3-yl)-1-piperidinyl]propoxy]-3-methoxyphenyl]-2-hydroxyethanone; 4-[3-[4-(6-fluoro-1,2-benzisoxazol-3-yl)-1-piperidinyl]propoxy]-3-hydroxy-α-methylbenzene methanol; 4-[3-[4-(6-fluoro-1,2-benzisoxazol-3-yl)-1-piperidinyl]propoxyl-2-hydroxy-5-methoxy-α-methylbenzenemethanol; 1-[4-[3-[4-(6-fluoro-1,2-benzisoxazol-3-yl)-1-piperidinyl]propoxy]-2-hydroxy-5-methoxyphenyl]ethanone; and 1-[4-[3-[4-(6-fluoro-1,2-benzisoxazol-3-yl)-1-piperidinyl]propoxy]-2,5-dihydroxyphenyl]ethanone. See U.S. Pat. No. 5,364,866, and International Patent Application Publication Nos. WO9309276 and WO9511680.

Previous studies have investigated associations between iloperidone efficacy and polymorphisms in genes and gene regions including CFTR, NPAS3, XKR4, TNR, GRIA4, GFRA2, and NUDT9P1. These associations are described in, e.g., U.S. Pat. Nos. 9,328,387, 9,458,507, and 9,080,214. Additionally, associations between CYP2D6 and KCNQ1 genotypes and changes in QT interval following the administration of iloperidone are described in U.S. Pat. Nos. 8,586,610, 9,138,432, 8,999,638, and 9,157,121. Such findings relating to the efficacy of iloperidone aid in selection of the most optimal drug and dosage regimen for a particular patient. This in turn aids in safe and effective treatment of psychotic symptoms, diseases, and disorders, with less trial and error.

SUMMARY OF THE INVENTION

In a first aspect of the invention, an improvement is provided in a method consisting of administering to a schizophrenia patient an amount of an active pharmaceutical ingredient (API), effective to treat said patient's schizophrenia. In various embodiments, the active pharmaceutical ingredient (API) may be an antipsychotic agent, which may further be a typical antipsychotic agent such as, e.g., chlorpromazine, fluphenazine, haloperidol, perphenazine, thioridazine, or thiothixene, or may be an atypical antipsychotic agent such as, e.g., aripiprazole, asenapine, clozapine, iloperidone, lurasidone, olanzapine, paliperidone, quetiapine, risperidone, or ziprasidone. In other embodiments, the API may be an mGluR5 agonist. The improvement comprises selecting the patient for treatment with the API based upon a determination that said patient's gene sequence includes a mutation in PPEF2. In various embodiments, the mutation in PPEF2 is a loss of function mutation. More particularly, the mutation may be a missense mutation such as R86H, or a stopgain mutation such as PPEF2:NM_006239:exon3:c.G135A:p.W45X. In certain embodiments, the atypical antipsychotic agent may be iloperidone, a metabolite of iloperidone, or a pharmaceutically acceptable salt of iloperidone or the metabolite thereof, and in particular, the amount of iloperidone may be between 12 mg/day and 24 mg/day, depending on factors including but not limited to severity of symptoms, patent genotype at various loci relevant to the disease or metabolism of the drug, and other considerations.

In a second aspect of the invention, a method is provided for treating a schizophrenia patient with an active pharmaceutical ingredient (API), comprising: identifying the patient's genotype at the PPEF2 locus; and if the patient carries a mutation in PPEF2, then internally administering the API to the patient at a dose of 12-24 mg/day depending on factors including but not limited to those described above. The step of identifying may further comprise: obtaining or having obtained a biological sample from the patient; and performing or having performed a genotyping assay on the biological sample to determine the patient's PPEF2 genotype. In various embodiments, the mutation in PPEF2 is a loss of function mutation. More particularly, the mutation may be a missense mutation such as R86H, or a stopgain mutation such as PPEF2:NM_006239:exon3:c.G135A:p.W45X. In various embodiments, the API may be an antipsychotic agent, which may further be a typical antipsychotic agent such as, e.g., chlorpromazine, fluphenazine, haloperidol, perphenazine, thioridazine, or thiothixene, or may be an atypical antipsychotic agent such as, e.g., aripiprazole, asenapine, clozapine, iloperidone, lurasidone, olanzapine, paliperidone, quetiapine, risperidone, or ziprasidone. In other embodiments, the API may be an mGluR5 agonist. In certain embodiments, the atypical antipsychotic agent may be iloperidone, a metabolite of iloperidone, or a pharmaceutically acceptable salt of iloperidone or the metabolite thereof, and in particular, the amount of iloperidone may be between 12 mg/day and 24 mg/day, depending on factors including but not limited to severity of symptoms, patent genotype at various loci relevant to the disease or metabolism of the drug, and other considerations.

DETAILED DESCRIPTION

Figure 1:
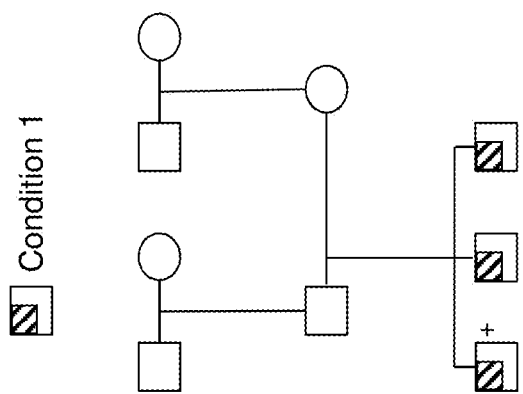
FIG. 1 illustrates the pedigree ("pedigree 1") of a family included in the study described in Example 1.
Figure 2:
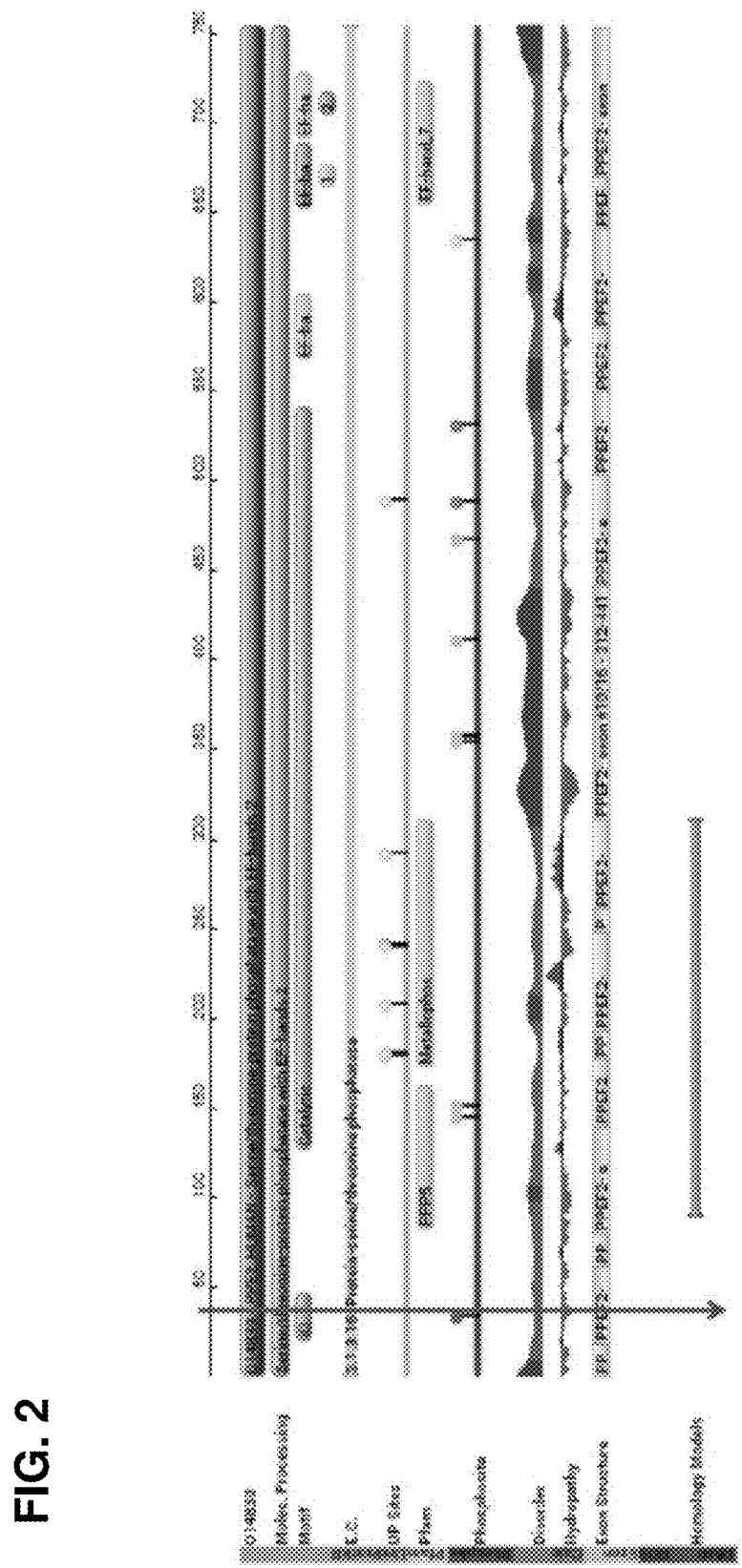
FIG. 2 illustrates results of the study described in Example 1.
Figure 3:
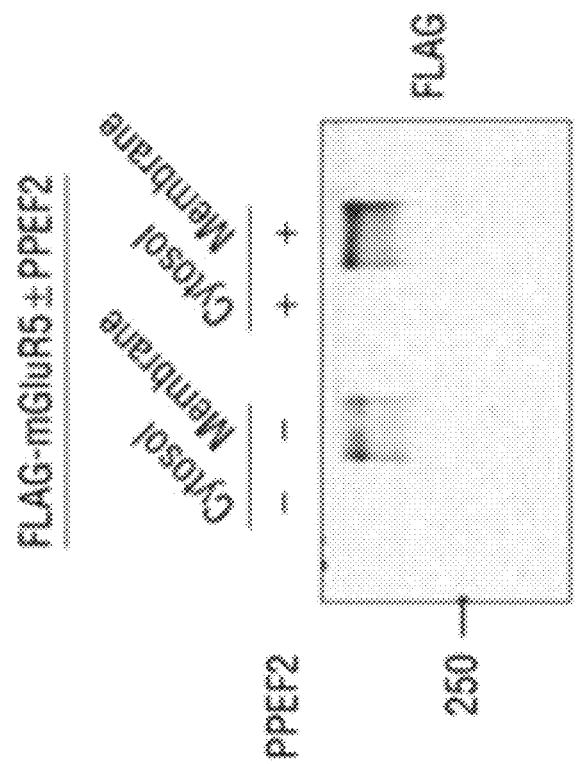
FIG. 3 illustrates an immunoblot showing influence of PPEF2 on FLAG-tagged metabotropic glutamate receptor subtype 5 (mGluR5) on cotransfection in the presence of the 3,5 dihydroxyphenylglycine agonist in HEK293 cells, courtesy of Timms, et al. (2013).

Various embodiments of the invention provide improved methods for treating psychotic diseases, disorders, and symptoms thereof using an active pharmaceutical ingredient (API) that may be an antipsychotic agent or an mGluR5 agonist, selecting patients for such treatment on the basis of identifying those whose gene sequences include genetic variants identified herein, and predicting the likelihood that a particular patient will respond significantly and favorably to treatment. In various embodiments, the psychotic disease being treated may be schizophrenia.

A method is provided in which an API administered to a patient suffering from schizophrenia in an amount effective to treat said patient's schizophrenia, in which the patient is selected on the basis of genotype at the PPEF2 locus. In particular embodiments, the patient be selected on the basis of having a stopgain mutation in PPEF2, and the mutation may more particularly be the LOF PPEF2:NM_006239: exon3:c.G135A:p.W45X variant. In other embodiments, the patient may be selected for treatment on the basis of having a missense variant (R86H) in PPEF2. In various embodiments, the API may be an antipsychotic agent, which may further be a typical antipsychotic agent such as, e.g., chlorpromazine, fluphenazine, haloperidol, perphenazine, thioridazine, or thiothixene, or may be an atypical antipsychotic agent such as, e.g., aripiprazole, asenapine, clozapine, iloperidone, lurasidone, olanzapine, paliperidone, quetiapine, risperidone, or ziprasidone. In other embodiments, the API may be an mGluR5 agonist. In certain embodiments, the atypical antipsychotic agent may be iloperidone, a metabolite of iloperidone, or a pharmaceutically acceptable salt of iloperidone or the metabolite thereof, and in particular, the amount of iloperidone may be between 12 mg/day and 24 mg/day, depending on factors including but not limited to severity of symptoms, patent genotype at various loci relevant to the disease or metabolism of the drug, and other considerations.

A method is further provided for treating schizophrenia in a patient with an API as defined above, including identifying whether the patient's gene sequence includes a variant in PPEF2. The identifying step may include a number of different methods of identification. In one aspect, identifying a genotype may include performing a genotyping assay on a biological sample collected from the patient to be treated. The biological sample may include, e.g., blood, serum, saliva, urine, et al. as is known in the art. The performance of such an assay may include steps such as, e.g., extracting genomic DNA or mRNA from the biological sample, and sequencing DNA derived from the extracted genomic DNA or from the extracted mRNA, including amplifying a gene region in the extracted genomic DNA or mRNA to prepare a DNA sample enriched with DNA from the relevant gene region. The DNA sample may then be hybridized to nucleic acid probes to determine whether the patient has a genotype of interest.

In some embodiments, identifying a genotype may include reviewing a patient's medical history, result report, or other document containing the result of a previously-performed assay or genetic test. In still further aspects, the identifying may include causing or requesting an assay to be performed by another individual, or causing or requesting the review of the patient's medical history, result report, or other document containing the result of a previously-performed assay or genetic test.

In any event, the method includes identifying the patient's PPEF2 genotype, for example, determining whether the patient carries, e.g., a missense variant such as R86H, or a stopgain mutation such as the LOF variant, PPEF2: NM_006239:exon3:c.G135A:p.W45X. If the patient's genotype includes such a variant, then the patient may be predisposed to schizophrenia, and in particular may be predisposed to early onset of schizophrenia. In this instance, the patient may particularly benefit from treatment with the API, which may be, e.g., a typical antipsychotic agent such as chlorpromazine, fluphenazine, haloperidol, perphenazine, thioridazine, or thiothixene, an atypical antipsychotic agent such as aripiprazole, asenapine, clozapine, iloperidone, lurasidone, olanzapine, paliperidone, quetiapine, risperidone, or ziprasidone, or an mGluR5 agonist. In certain embodiments, the atypical antipsychotic agent may be iloperidone, a metabolite of iloperidone, or a pharmaceutically acceptable salt of iloperidone or the metabolite thereof, and in particular, the amount of iloperidone may be between 12 mg/day and 24 mg/day, depending on factors including but not limited to severity of symptoms, patent genotype at various loci relevant to the disease or metabolism of the drug, and other considerations. The method may include internally administering the API, for example iloperidone, to the patient at a dose of between 12 mg/day and 24 mg/day, e.g., 12 mg/day, 14 mg/day, 16 mg/day, 18 mg/day, 20 mg/day, 22 mg/day, or 24 mg/day. In various embodiments, enhanced monitoring may be indicated where the patient receives relatively larger doses of iloperidone, e.g., 20 mg/day, 22, mg/day, or 24 mg/day. In cases in which the patient has a genotype that does not include one of the foregoing variants, the patient may not be genetically predisposed to schizophrenia, or more particularly may not be predisposed to early onset schizophrenia. In this instance, the patient's psychotic symptoms may be treated using a different treatment regimen, which may include administration of a different drug.

The foregoing methods collectively aid physicians in prospectively identifying patients who are at increased risk of developing schizophrenia, particularly early onset schizophrenia, and will particularly benefit from treatment with an API such as, e.g., iloperidone. The ability to identify patients who are likely to benefit from treatment prior to commencement of treatment itself provides a meaningful benefit to patients and practitioners as it reduces the amount of trial and error that a patient must endure before identifying an effective treatment regimen to gain and maintain control of psychotic symptoms.

An effective amount of an API such as, e.g., iloperidone or an active metabolite thereof may be administered to a subject animal (typically a human but other animals, e.g., farm animals, pets and racing animals, can also be treated) by a number of routes. An effective amount is an amount that during the course of therapy will have a preventive or ameliorative effect on a psychotic disorder, such as schizophrenia, or a symptom thereof, or of bipolar disorder. An effective amount may quantitatively vary depending upon, for example, the patient, the severity of the disorder or symptom being treated, and the route of administration.

It will be understood that the dosing protocol including the amount of API, for example iloperidone, a metabolite of iloperidone, or a pharmaceutically acceptable salt of iloperidone or the metabolite thereof actually administered will be determined by a physician in the light of the relevant circumstances including, for example, the condition to be treated, the chosen route of administration, the age, weight, and response of the individual patient, and the severity of the patient's symptoms. Patients should be monitored for possible adverse events.

For therapeutic use, the API, for example, iloperidone, a metabolite of iloperidone, or a pharmaceutically acceptable salt of iloperidone or the metabolite thereof will normally be administered as a pharmaceutical composition as the (or an) essential active ingredient at least one such compound in association with a solid or liquid pharmaceutically acceptable carrier and, optionally, with pharmaceutically acceptable adjuvants and excipients employing standard and conventional techniques.

Pharmaceutical compositions useful in the practice of this invention include suitable dosage forms for oral, parenteral (including subcutaneous, intramuscular, intradermal and intravenous), transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions may be prepared by conventional techniques appropriate to the desired preparation containing appropriate amounts of API, for example, iloperidone or an active metabolite thereof. See, for example, Remington's Pharmaceutical Sciences, Mack Publishing Company, Easton, Pa., 17th edition, 1985.

In making pharmaceutical compositions for use in the invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form. The term "unit dosage form" refers to physically discrete units suitable as unitary dosages for human subjects and other mammals, each unit containing a predetermined quantity of active material calculated to produce the desired prophylactic or therapeutic effect over the course of a treatment period, in association with the required pharmaceutical carrier.

Iloperidone and its active metabolites can also be formulated in a controlled release form, e.g., delayed, sustained, or pulsatile release. Various formulations and methods of administering iloperidone and/or its derivatives have been described. For example, U.S. Pat. Nos. 8,227,488; 8,293,765; and 8,614,232 describe an injectable depot formulation comprising iloperidone crystals; and microencapsulated depot formulations of iloperidone and a polyglycolide polylactide glucose star polymer are described in U.S. Pat. Nos. 7,767,230 and 8,815,293.

Example 1

An in-patient, open label, sequential dose escalation study is conducted to evaluate the safety, tolerability, and pharmacokinetics of iloperidone long active injectable (LAI). Up to 27 study participants enroll, each of whom may be male or female, is aged 18 to 65 years (inclusive), is diagnosed with schizophrenia according to DSM-V criteria for at least one year, and is symptomatically stable. The study participants include a family with three (3) affected male individuals that developed schizophrenia at 9, 11, and 17 years of age respectively (FIG. 1), indicating a strong genetic predisposition for schizophrenia within the family.

A blood sample is drawn from each participant at the screening visit, and whole genome sequencing (WGS) is performed in order to detect genetic factors predisposing individuals to early onset schizophrenia. WGS is performed on DNA samples obtained from study participants using Illumina HiSeq X instruments, enabling sequencing of up to 18,000 30× human whole genomes. Whole genome data are processed on New York Genome Center (NYGC) automated pipelines. Paired-end 150 bp reads are aligned to the GRCh37 human reference (BWA-MEM v0.7.8) and processed with GATK best practices workflow (GATK v.3.4.0). Sequencing results are annotated using ANNOVAR software. Normal population allelic frequencies are extracted from Exome Aggregation Consortium (ExAC) and Genome Aggregation Database (gnomAD). LOF fold change analysis is conducted vs. gnomAD frequencies. Finally, WGS Loss of Function analysis of the mutation landscape and functional analysis of PPEF2 are conducted.

Results

Whole genome sequencing in XX subjects with schizophrenia identify a novel rare stopgain mutation in PPEF2 (Protein Phosphatase With EF-Hand Domain 2) in a family with 3 affected individuals. The LOF PPEF2:NM_006239: exon3:c.G135A:p.W45X has a minor allele frequency (MAF) of 2.83E-05 in ExAC and has a combined annotation dependent deletion (CADD) score of 37 (~1/30000 carrier). Population allelic frequencies are shown in Table 1.

TABLE 1

Population Frequencies

| Population | Allele count | Allele number | Number of homozygotes | Allele frequency |
|---|---|---|---|---|
| African | 3 | 16240 | 0 | 0.0001847 |
| Other | 1 | 6124 | 0 | 0.0001633 |
| Latino | 0 | 34570 | 0 | 0.000 |
| Ashkenazi Jewish | 0 | 10078 | 0 | 0.000 |
| East Asian | 0 | 18384 | 0 | 0.000 |
| European (Finnish) | 0 | 21646 | 0 | 0.000 |
| European (non-Finnish) | 0 | 113624 | 0 | 0.000 |
| South Asian | 0 | 30616 | 0 | 0.000 |
| Male | 3 | 135854 | 0 | 0.00002208 |
| Female | 1 | 115428 | 0 | 0.000008663 |
| Total | 4 | 251282 | 0 | 0.00001592 |

DISCUSSION

PPEF2 encodes a neuronally expressed protein phosphatase that binds calmodulin. PPEF2 appears to be involved in the N-methyl-D-aspartate receptor network by affecting the levels of certain brain nerve cell signaling mediators. Specifically, HEK293 cells transfected with PPEF2 demonstrate increased levels of mGluR5 in the presence of an mGluR5 agonist, suggesting that disturbance of PPEF2 could lower mGluR5 membrane levels.

A missense substitution was previously reported for a single family with multiple affected individuals with schizophrenia. Intriguingly, all affected individuals in a pedigree (A. E. Timms, et al., "Support for the N-methyl-D-aspartate receptor hypofunction hypothesis of schizophrenia from exome sequencing in multiplex family," JAMA Psychiatry. vol. 70, no. 6(Print), pp. 582-90 (June 2013)) share a missense variant (R86H) in PPEF2. Given that mGluR5 and PPEF2 both bind calmodulin, they investigated whether PPEF2 expression influences mGluR5 levels. The observation that HEK293 cells transfected with PPEF2 demonstrate increased levels of mGluR5 in the presence of the mGluR5 agonist suggests that disturbance of PPEF2 could lower mGluR5 membrane levels. This mutation supports the N-Methyl-D-Aspartate Receptor Hypofunction Hypothesis of Schizophrenia from WGS data.

Whole genome sequencing delineates a novel deleterious variant in PPEF2 as a likely genetic risk factor for schizophrenia in a family with three (3) affected male individuals. This finding provides useful information for characterizing a rare mutation that may predispose individuals to developing schizophrenia and help elucidate the pathway leading to this disorder as well as potential new therapeutic targets. Additional genomic screens that stratify patients based on the affected genetic pathways may better guide the most effective treatments.

The foregoing description of various aspects of the invention has been presented for purposes of illustration and description. It is not intended to be exhaustive or to limit the invention to the precise form disclosed, and modifications and variations are possible. Such modifications and variations that may be apparent to a person skilled in the art are intended to be included within the scope of the invention as defined by the accompanying claims.

We claim:

1. In a method consisting of administering to a schizophrenia patient an amount of an active pharmaceutical ingredient (API) effective to treat said patient's schizophrenia, wherein the API is iloperidone, a metabolite of iloperidone, or a pharmaceutically acceptable salt of iloperidone or the metabolite thereof, the improvement comprising:
    selecting said patient for treatment based upon a determination that said patient's gene sequence includes a mutation in PPEF2.

2. The improvement of claim 1, in which the mutation in PPEF2 is a loss of function mutation.

3. The improvement of claim 1, in which the mutation in PPEF2 is a missense mutation that is R86H.

4. The improvement of claim 1, wherein the mutation is a stopgain mutation that is PPEF2:NM 006239:exon3: c.G135A:p.W45X.

5. The improvement of claim 1, wherein the API is iloperidone, and the amount of iloperidone is 12 mg/day to 24 mg/day.

6. A method for treating a schizophrenia patient, comprising:
    identifying the patient's genotype at the PPEF2 locus; and
    if the patient has a genotype including a mutation in PPEF2, then internally administering an active pharmaceutical ingredient (API) to the patient, wherein the API is iloperidone, a metabolite of iloperidone, or a pharmaceutically acceptable salt of iloperidone or the metabolite thereof.

7. The method of claim 6, in which the mutation in PPEF2 is a loss of function mutation.

8. The method of claim 6, in which the mutation in PPEF2 is a missense mutation, and wherein the missense mutation in PPEF2 is R86H.

9. The method of claim 6, wherein the mutation is a stopgain mutation, and wherein the stopgain mutation is PPEF2:NM_006239:exon3:c.G135A:p.W45X.

10. The method according to claim 6, wherein the step of identifying comprises:
    obtaining or having obtained a biological sample from the patient; and
    performing or having performed a genotyping assay on the biological sample to determine the patient's PPEF2 genotype.

11. In a method consisting of administering to a schizophrenia patient an amount of an active pharmaceutical ingredient (API) effective to treat said patient's schizophrenia, the improvement comprising:

selecting said patient for treatment based upon a determination that said patient's gene sequence includes a loss of function mutation in PPEF2.

12. The improvement of claim 11, wherein the API comprises:
   a) an atypical antipsychotic agent, wherein the atypical antipsychotic agent is selected from the group consisting of: aripiprazole, asenapine, clozapine, iloperidone, a metabolite of iloperidone, a pharmaceutically acceptable salt of iloperidone, a pharmaceutically acceptable salt of the metabolite of iloperidone, lurasidone, olanzapine, paliperidone, quetiapine, risperidone, and ziprasidone;
   b) a typical antipsychotic agent, wherein the typical antipsychotic agent is selected from the group consisting of: chlorpromazine, fluphenazine, haloperidol, perphenazine, thioridazine, and thiothixene; or
   c) an mGluR5 agonist.

13. The improvement of claim 11, wherein the API is iloperidone, and the amount of iloperidone is 12 mg/day to 24 mg/day.

14. In a method consisting of administering to a schizophrenia patient an amount of an active pharmaceutical ingredient (API) effective to treat said patient's schizophrenia, the improvement comprising:
   selecting said patient for treatment based upon a determination that said patient's gene sequence includes a stopgain mutation in PPEF2.

15. The improvement of claim 14, wherein the stopgain mutation is PPEF2:NM_006239:exon3:c.G135A:p.W45X.

16. The improvement of claim 14, wherein the API comprises:
   a) an atypical antipsychotic agent, wherein the atypical antipsychotic agent is selected from the group consisting of: aripiprazole, asenapine, clozapine, iloperidone, a metabolite of iloperidone, a pharmaceutically acceptable salt of iloperidone, a pharmaceutically acceptable salt of the metabolite of iloperidone, lurasidone, olanzapine, paliperidone, quetiapine, risperidone, and ziprasidone;
   b) a typical antipsychotic agent, wherein the typical antipsychotic agent is selected from the group consisting of: chlorpromazine, fluphenazine, haloperidol, perphenazine, thioridazine, and thiothixene; or
   c) an mGluR5 agonist.

17. The improvement of claim 14, wherein the API is iloperidone, and the amount of iloperidone is 12 mg/day to 24 mg/day.

18. A method for treating a schizophrenia patient, comprising:
   identifying the patient's genotype at the PPEF2 locus; and
   if the patient has a genotype including a loss of function mutation in PPEF2, then internally administering an active pharmaceutical ingredient (API) to the patient.

19. The method of claim 18, wherein the API comprises:
   a) an atypical antipsychotic agent, wherein the atypical antipsychotic agent is selected from the group consisting of: aripiprazole, asenapine, clozapine, iloperidone, a metabolite of iloperidone, a pharmaceutically acceptable salt of iloperidone, a pharmaceutically acceptable salt of the metabolite of iloperidone, lurasidone, olanzapine, paliperidone, quetiapine, risperidone, and ziprasidone;
   b) a typical antipsychotic agent, wherein the typical antipsychotic agent is selected from the group consisting of: chlorpromazine, fluphenazine, haloperidol, perphenazine, thioridazine, and thiothixene; or
   c) an mGluR5 agonist.

20. The method according to claim 18, wherein the step of identifying comprises:
   obtaining or having obtained a biological sample from the patient; and
   performing or having performed a genotyping assay on the biological sample to determine the patient's PPEF2 genotype.

21. A method for treating a schizophrenia patient, comprising:
   identifying the patient's genotype at the PPEF2 locus; and
   if the patient has a genotype including a stopgain mutation in PPEF2, then internally administering an active pharmaceutical ingredient (API) to the patient.

22. The method of claim 21, wherein the API comprises:
   a) an atypical antipsychotic agent, wherein the atypical antipsychotic agent is selected from the group consisting of: aripiprazole, asenapine, clozapine, iloperidone, a metabolite of iloperidone, a pharmaceutically acceptable salt of iloperidone, a pharmaceutically acceptable salt of the metabolite of iloperidone, lurasidone, olanzapine, paliperidone, quetiapine, risperidone, and ziprasidone;
   b) a typical antipsychotic agent, wherein the typical antipsychotic agent is selected from the group consisting of: chlorpromazine, fluphenazine, haloperidol, perphenazine, thioridazine, and thiothixene; or
   c) an mGluR5 agonist.

23. The method according to claim 21, wherein the step of identifying comprises:
   obtaining or having obtained a biological sample from the patient; and
   performing or having performed a genotyping assay on the biological sample to determine the patient's PPEF2 genotype.

* * * * *